United States Patent
Sullivan

Patent Number: 5,989,193
Date of Patent: Nov. 23, 1999

[54] DEVICE AND METHOD FOR DETECTING AND RECORDING SNORING

[75] Inventor: Colin Edward Sullivan, New South Wales, Australia

[73] Assignee: Somed Pty Limited, New South Wales, Australia

[21] Appl. No.: 08/952,615

[22] PCT Filed: May 20, 1996

[86] PCT No.: PCT/AU96/00306

§ 371 Date: Feb. 19, 1998

§ 102(e) Date: Feb. 19, 1998

[87] PCT Pub. No.: WO96/36279

PCT Pub. Date: Nov. 21, 1996

[30] Foreign Application Priority Data

May 19, 1995 [AU] Australia .................. PN3048

[51] Int. Cl.$^6$ .......................................... A61B 5/08
[52] U.S. Cl. .................. 600/534; 600/529; 600/586
[58] Field of Search .................. 600/483, 484, 600/529, 532, 533, 534, 538, 586

[56] References Cited

U.S. PATENT DOCUMENTS

| | | |
|---|---|---|
| 4,146,885 | 3/1979 | Lawson, Jr. ............................ 600/534 |
| 4,320,766 | 3/1982 | Alihanka et al. ...................... 600/484 |
| 4,509,527 | 4/1985 | Fraden .................................. 600/534 |
| 4,657,026 | 4/1987 | Tagg .................................... 600/534 |
| 4,686,999 | 8/1987 | Snyder et al. ......................... 600/534 |
| 4,830,008 | 5/1989 | Meer .................................... 600/534 |
| 4,848,360 | 7/1989 | Palsgrad et al. ...................... 600/586 |
| 4,862,144 | 8/1989 | Tao ...................................... 600/534 |
| 5,099,702 | 3/1992 | French .................................. 600/534 |

*Primary Examiner*—Cary O'Connor
*Assistant Examiner*—Charles Marmor, II
*Attorney, Agent, or Firm*—Jordan and Hamburg LLP

[57] ABSTRACT

A device and method for detecting and recording the snoring of a patient. The device comprises a piezoelectric sensor, placed below a sleeping patient on a mattress, which generates signals representative of the sub-audible vibrations of the patient's airway which are present during a snore. The signals generated by the sensor can be amplified by an amplifier and processed by a signal processing circuit. The sensor can also generate signals representative of the patient's breathing cycle and general movement of the patient. The signal processing circuit can be adapted to discriminate the signals generated by the sensor and then output these signals for analysis. The output can be used to determine the presence of snoring by the patient and the snoring pattern can also be used to detect episodes of obstructive sleep apnea.

26 Claims, 5 Drawing Sheets

DEVICE AND METHOD FOR DETECTING AND RECORDING SNORING

FIELD OF THE INVENTION

The present invention relates to a device and method for detecting and recording the snoring of a patient.

BACKGROUND ART

There are a number of diseases and disorders which only manifest their presence in sleep or at least markedly worsen during sleep. One sleep linked disorder is obstructive sleep apnea. A patient suffering this disorder undergoes while asleep repeated episodes of obstruction of their upper airway. During these episodes of obstruction there is a period, which can typically range between 10–40 seconds, when there is no airflow through the airway into the lungs of a patient. This state usually terminates due to arousal of the patient.

In mild cases of sleep apnea, a sufferer may only undergo a few episodes of obstruction over a night of 6–8 hours of sleep. In more severe cases, the episodes can occur repeatedly with tests showing that some sufferers undergo 400–500 episodes of obstruction in a single night's sleep. Such high levels of obstruction and the resulting repeated falls in oxygen level to the brain can lead to major health problems, and sufferers are known to have increased mortality, probably because of increased morbidity due to cardiovascular diseases and stroke. Sufferers also exhibit high levels of daytime sleepiness which increases the risk of a sufferer being involved in a traffic or industrial accident. It is now recognised that at any one time about 10% of males and about 5% of females suffer from some form of sleep apnea.

Obstructive sleep apnea is now widely recognized by its array of daytime symptoms including daytime sleepiness and also by witnessed episodes of "stop breathing" by a bed partner. Heavy snoring is, however, the most common and characteristic sign of sleep apnea.

Snoring is almost universally known and is characterised by noise generated in the throat of a sleeping individual. Snoring is in fact so tightly coupled with sleep that its presence is a positive and diagnostic indication that an individual is asleep.

Snoring is a noise which is typically generated by vibration of the air conduction tube at the level of the throat. It usually occurs during inspiration (breathing in) but sometimes occurs during expiration (breathing out) and sometimes during both phases of the sleeping cycle. Snoring occurs when, with sleep, there is a loss of muscle tone in the muscles of the throat which are needed to keep the throat open. This loss in muscle tone narrows the air passages leading to inadequate levels of airflow into the lungs. This drop in airflow is detected and the body's reflexes automatically produce increased efforts to breathe. These increased efforts produce greater degrees of suction pressure in the air passages which then in turn cause the walls of the throat to vibrate and flutter. Snoring commonly originates in the oropharyngeal area of the throat. This is the region where the cavity of the mouth and a cavity from the nasal airway join to form one tube at the oral region of the pharynx. In this region, the soft palate which is a mobile structure which hangs down from the roof of the mouth in the back of the throat, acts to determine which of the two pathways are connected to the breathing tube. Most commonly, snoring is generated when the soft palate flutters. This fluttering leads to pressure oscillations within the airway and sounds are then generated when other structures in and around the airway are vibrated producing harmonics which can be heard.

The underlying physical properties of snoring start, therefore, when the airway flutters at a critical location resulting in the suction pressure in the airway also oscillating. This pressure oscillation radiates in all directions, including both outwards through the nose and mouth, and inwards back into the lungs and chest wall. The pressure oscillation causes other tissues to oscillate and vibrate and harmonics are formed causing audible sound.

The audible sound which is widely known a snoring is the result of vibration of a range of tissues and the harmonics which are then formed. The sound is the result of complex movements end various filtering by nasal structures. In contrast, the underlying pressure oscillations of the airway which leads to these sounds are inaudible. The easiest way to demonstrate the existence of the underlying pressure oscillation is for an individual to voluntarily snore. This can be done with a little training; the throat is relaxed, the mouth opened, and then strong inspiratory efforts are made. Doing this, most people can make their soft palate flutter and thus generate snoring sounds. When the nose is observed during this action, the walls of the nasal entry can be seen to oscillate as a result of the low frequency inaudible pressure wave being transmitted along the airway.

While snoring is the most common and characteristic symptom of sleep apnea it does not necessarily follow that if a person is a heavy snorer they will also suffer sleep apnea. A report an heavy snoring can, therefore, alone not provide enough information to positively diagnose or exclude the existence of sleep apnea. When a subject develops sleep apnea, however, the pattern of snoring typically changes. Instead of the sound of regular rhythmical snoring occurring at a time sequence identical to the breathing cycle there are typically bursts of a few loud snoring breaths, separated by a longer period of silence of 15–50 seconds indicative of obstruction. This sequence usually occurs in a regularly occurring pattern over many minutes or even hours.

The recognition of this characteristic pattern of snoring has been used to diagnose the presence of adult sleep apnea. There are many devices which are based on the recording of sound and many of these are used as diagnostic devices to identify snoring. These devices range from microphones being placed in a room of a sufferer or on the throat or even in a hearing aid placed in the ear of a sufferer. Some devices use sound analysis systems to characterise the sound signature and then to count the number of snores or the number of apneas in a night of recording. Many doctors also ask their patients to record their own snoring and then return the tapes so that they may listen for the characteristic pattern of sounds. This method is very good as it utilizes the physician's car as the analysis system which can readily detect the typical sound of snoring and then the typical pattern of broken snoring indicative of sleep apnea. It is, however, an impractical method as the audio recordings have to be replayed and to date there has been no efficient way of providing quantitative analysis.

A particular problem with recording sound alone is that it is also difficult to separate other sounds such as someone talking, a door slamming, the radio or television in the background, a car or truck passing outside, or even someone else's snoring in the room. To counter this problem, an independent measure of respiration is typically used to timelock the sound of snoring to the breathing cycle. Typical devices for measuring respiration are thermistors and pressure transducers that are attached to the patient and measure airflow at the mouth or nose or other devices also attached to the patient which monitor chest movement.

DISCLOSURE OF THE INVENTION

The present invention consists in a device for detecting the snoring of a patient comprising signal processing means having signal receiving means to receive electrical signals generated by a pressure or acceleration detector, the detector being capable of generating a first electrical signal representative of sub-audible vibrations of the airway of the patient which are present during a snore.

In a further aspect, the present invention consists in a method for detecting the snoring of a patient comprising the steps of placing a pressure or acceleration detector in position relative to a patient for a period of time while the patient is asleep, producing from the detector a first electrical signal representative of sub-audible vibrations in the airway of the patient which are present during a snore.

In a preferred embodiment of the invention, the detector is capable of generating a second electrical signal representative of the breathing cycle of the patient. While the breathing rate of a human can vary significantly due to such factors as illness or exertion, the frequency of the breathing cycle of a sleeping human typically lies in the range of greater than 0 Hz and less than or equal to 2 Hz. The advantage of having the detector generate a second electrical signal representative of the breathing cycle is that the occurrence of the sub-audible vibrations can be time-locked to the breathing cycle. If the peaks in the first electrical signal occur during inspiration or expiration, this provides confirmation that the first electrical signal being received is in fact indicative of the sub-audible vibrations prevent in the airway during a snore.

In one embodiment of the invention, the detector can also be capable of generating a third electrical signal representative of the movement of the patient during sleep. Such movements might include the patient rolling over, turning of the head and large or small movements of the legs and arms. This third signal can be used to provide further discrimination between signals representing vibration of the patient's airway during a snore and other noises or movements by the patient that will result in signals being generated by the detector.

The pressure or acceleration detector can be placed on or under the mattress of a bed on which the patient will sleep. This arrangement is particularly advantageous as there is no discomfort caused to the patient by the attachment of any sensors. This arrangement also avoids the high risk of detachment or disconnection of sensors attached to the patient during the long hours of sleep. The detector could also be attached to the bed frame or incorporated in a pillow as well as or instead of on or under the mattress. The detector may be attached to a hearing aid placed in the ear of the patient.

The pressure detector can comprise a piezoelectric transducer while the accelerometer can comprise an integrated circuit containing a floating piezoelectric transducer. In a preferred embodiment, the detector comprises one or a plurality of sheets of piezoelectric plastics material such as polyvinilidene fluoride (hereinafter called PVDF) or an analogue or family derivative thereof. PVDF is an ideal material for this invention as it has a potential frequency response from sub Hertz (ie less than one cycle per second) to kiloHertz levels. In addition, the material is highly sensitive, producing relatively larger voltages in response to extremely small movements. It can, for example. act as a highly sensitive microphone detecting low levels of sound pressure. In this invention, the microphone property of PVDF is used to essentially "listen" to the sub-audible vibrations of the patient's airway causing the characteristic audible sound of snoring. The invention takes advantage of the physical properties of this plastic, which is robust, to cheracterise the vibration of the airway during snoring and the breathing cycle of the patient, to identify the dominant frequency components of these actions and, by comparison, to positively separate each action thus allowing the generation of electrical signals which can be recorded and identified as that of the vibration of the airway and breathing movements.

The piezoelectric plastics material may consist of a layer of this material attached to a firm rubber or plastic backing sheet, with or without an air space. Multiple layers of the piezoelectric material throughout a mattress may also be utilized where appropriate.

The detector detects movements of low frequency (ie: 0–2 Hertz) which can be digitally processed and amplified to give a signal representative of the breathing cycle (inspiration and expiration) of the patient. If the patient is snoring, the detector will also detect the fluttering sub-audible vibrations of the patients airway which are the underlying cause of the audible sound of snoring. These vibrations, which typically occur between 10–100 Hertz, are also digitally processed and amplified to give a signal representative of the fluttering vibrations in the airway which are indicative of snoring in the patient.

These signals may then be displayed in real time to allow a clinician to monitor if snoring is occurring and, if so, to determine the snoring pattern and the intensity of that snoring. The signals may also be stored and processed to produce an output for later analysis. The first and second signals could also be compared by a comparator means which would compare the first and second electrical signals and produce an output indicative of the comparison. For example, if on comparison the first electrical signal does not coincide with inspiration or expiration as determined from the measured breathing cycle, the comparator means could indicate that the measured first electrical signal is in fact not representative of airway vibrations.

On later analysis, the measured snoring pattern can also be compared with the breathing cycle to determine if partial upper airway obstruction or apnea is occurring. The most common apnea is obstructive apnea in which there is no airflow through the airway. The present device could readily identify or allow identification of such apneas. In a typical apnea episode, there will be cycles in which there are a series of inspirations with snoring detected, and then a series of inspiratory movements without snoring. The occurrence of an apnea episode will further be confirmed by analysis of the breathing movements against the closed airway and expiratory efforts being made to open the airway.

The present invention is particularly advantageous for those circumstances where a patient is suffering upper airway partial obstruction without the symptom of audible or at least heavy snoring. This is particularly the case for infants where upper airway partial obstruction is common but where snoring is not frequently identified. One reason for this is that the tissues around the airway of infants are very different to adults and so do not vibrate in the same way and therefore, do not produce the same audible sounds. The present invention is, therefore, suitable for the detection of upper airway dysfunction in infants which is not or at least not readily detected by methods or devices adapted to detect and monitor the audible sounds of snoring.

In a further embodiment of the invention, a sound transducer or microphone may be placed proximate the patient. The electrical signals generated from this transducer can be used to cross-check against the signals being received from the detector typically placed under the patient on the bed. The signal from the transducer could be used in two main ways. Firstly, if it detects a sound in the room concurrently with detection of any vibration in the airway, it can be assumed that a snore has been detected. Alternatively, it can be used to discriminate and reject other sounds present in the environment such as those caused by passing traffic and so eliminate consideration of these signals in the output provided by the device.

In a further aspect of the invention, the output from the device described herein can be used to provide a signal to control the operation of a positive airway pressure device, such as a nasal continuous positive airway pressure (nasal CPAP) device being used by the patient to alleviate the symptoms of sleep apnea. Nasal CPAP is the current treatment of choice for patients with sleep apnea. In this treatment, the patient breathes from a nose mask which has a slightly higher atmospheric pressure. This pressure in turn splints open the upper airway preventing snoring and apnea. Modern versions of this device adjust the pressure automatically according to the presence or absence of snoring. Detection of the sub-audible airway vibrations using the device described herein could provide a second crosscheck signal, or act as the major controlling signal for a nasal CPAP device. Another application of this principle would be the use of an implantable version of the sensor to provide the controlling signal for electrical pacing of the upper airway to treat snoring or apnea.

The recorded display of the output could utilize analogue and digital recorders and paper hard copies. A preferred method would record the output digitally on disk for later replay or in real time on a computer screen. The invention includes software for the display of long-term information.

BRIEF DESCRIPTION OF THE DRAWINGS

Hereinafter by way of example, a preferred embodiment of the invention is described with reference to the accompanying drawings, in which.

PREFERRED MODE OF THE INVENTION

Figure 1:
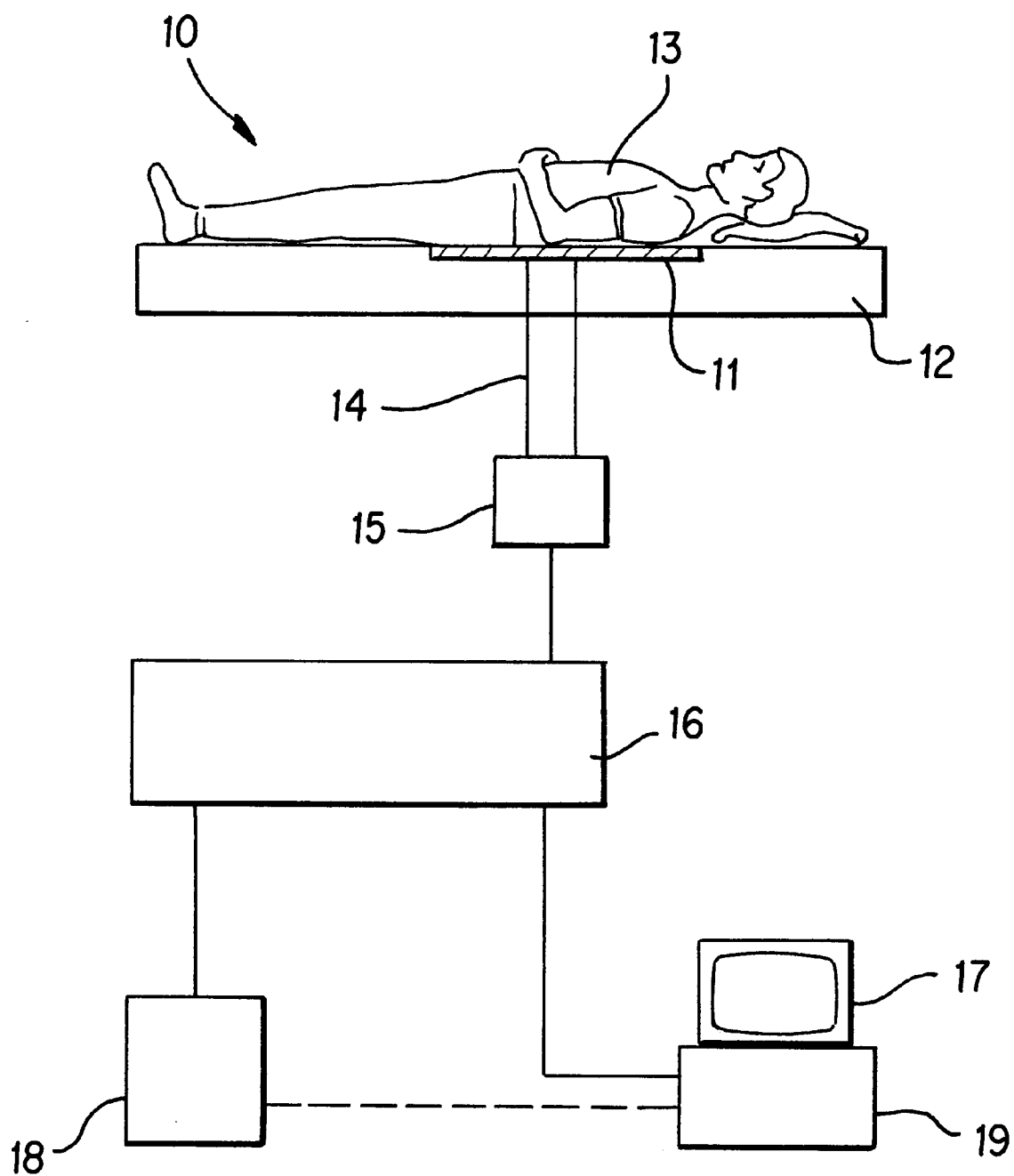
FIG. 1 is a diagrammatic view of a device for detecting and recording the snoring pattern of a patient according to the present invention.

A device for detecting and monitoring the snoring pattern of a patient is generally depicted as 10 in FIG. 1.

The device 10 includes a piezoelectric polyvinylidene fluoride (PVDF) sheet sensor 11 placed on a mattress 12 which supports a sleeping patient 13. The sensor 11 is placed on the mattress 12 such that the sensor 11 lies under the torso of the patient 13 when the patient is asleep on the mattress 12. The piezoelectric PVDF for use as the sensor 11 is available from a number of sources. The PVDF presently used by the inventor in experiments of the device 10 was provided in a special applications designs kit provided by AMP Incorporated, Valley Forge, Pa., United States of America, through the Australian distributor, Irendos Pty Limited of Glen Iris, Victoria, Australia.

The sensor 11 is connected by appropriate electrical leads 14 to an electronic amplifier device 15 which amplifies the voltage signals generated by the sensor 11. The amplified signals are then passed to a digital signal processing circuit 16 which is adapted to discriminate from the signals output by the sensor 11 signals representative of the breathing cycle of the patient and of episodes of airway vibrations which are the underlying cause of the audible sound of snoring.

The typical breathing cycle of a resting human is 12–14 breaths a minute. This breathing rate can increase or decrease significantly due to such factors as exertion and illness, it is, however, typical for the breathing cycle of a sleeping human to lie somewhere in the range 0.01–2 Hz. To detect the signals representative of the breathing cycle from the signals generated by the sensor 11, the signal processing circuit 16 is adapted to identify signals having a frequency in this range.

The underlying vibrations of the airway that lead to the audible sound of snoring are inaudible. Experiments have shown that the vibration frequency of the airway during a snore is typically in the range 10–100 Hz. The signal processing circuit 16 is, therefore, also adapted to identify signals having a frequency in this range.

The amplified signals output by the signal processing circuit 16 in the two frequency ranges can be fed to a display means 17 such as is depicted in FIG. 1. The display means can comprise a paper printer 18, a cathode ray oscilloscope and/or computer based display. In each case, the clinician monitoring the patient 13 could view the display in real-time to monitor the breathing cycle and, if present, episodes of airway vibration representative of snoring by the patient 13.

In an alternative embodiment, the signals output from the signal processing means 16 are stored in a digital recording system 19 and computer memory for later playback and analysis by the clinician.

The present application is particularly suitable for detecting the occurrence of sleep apnea in a patient where the patient reports with other telltale symptoms such as daytime sleepiness and complaints of heavy snoring. Prior to the patient laying on the mattress 12, the sensor 11 will be appropriately mounted on the mattress 12 and electically connected by leads 14 to the amplifier 15. The signal processing circuit 16 and the display means 17 will be turned on ready to monitor and record the signals detected by the sensor 11 during sleep. The patient 13 will then be allowed to lay on the mattress 12 and fall asleep in the normal manner. The device 10 is particularly advantageous as it does not require the attachment of special sensors to the skin of the patient which reduces clinician involvement and also reduces any potential discomfort to the patient 13.

The patient 13 will typically be monitored for an entire evening so as to ensure a good picture of the patient's sleeping cycle is available for review by the clinician. As discussed, the device 10 will monitor and store the breathing cycle of the patient 13. The device 10 also detects and stores episodes of snoring. The clinician by reviewing the print-out of signals in the frequency range 10–100 Hz can determine if snoring is occurring by watching for the characteristic vibration of the patient's airway on inspiration or expiration of the patient. If a signal is detected in the 10–100 Hz range which is not at inspiration or expiration, then this signal cannot relate to snoring and can be dismissed as a another noise created by the patient 13 or the surrounding environment. The advantage of detecting snoring is that it is a diagnostic indication to the clinician that the patient 13 is asleep. This has the advantage of not requiring the connection of further sensors to the patient such as EEG sensors which are typically used in the prior art to monitor if a person is actually asleep during sleep pattern studies such as studies attempting to detect episodes of sleep apnea in a patient.

Once snoring has been identified, the pattern of vibrations stored by the device 10 can be reviewed to determine the occurrence of episodes of sleep apnea. These episodes can be identified by gaps in the snoring cycle as when the airway obstructs, the patient 13 will make inspiratory movements without detection of a corresponding snore from the patient. Further confirmation that apnea is occurring will be provided by the breathing cycle signal output. When breathing movements are made against a closed airway, the pattern of movement changes so identifying an obstructive inspiratory effort. In addition, active expiratory efforts will often be made by the patient 13 in a reflex attempt to open the upper airway. These efforts typically generate small expiratory airflows with an accompanying vibration of the airway which are in turn detected by the sensor 11 and processed and stored by the signal processing circuit 16 and storage means, respectively.

Experiments undertaken by the inventor using the device 10 have shown that the device 10 can readily detect the occurrence of the airway vibrations which are present during a snore of the patient. The amplitude versus time print-outs depicted as FIGS. 2–5 represent small portions of the types of outputs that might be generated by the device 10 described herein during actual use.

Figure 2:
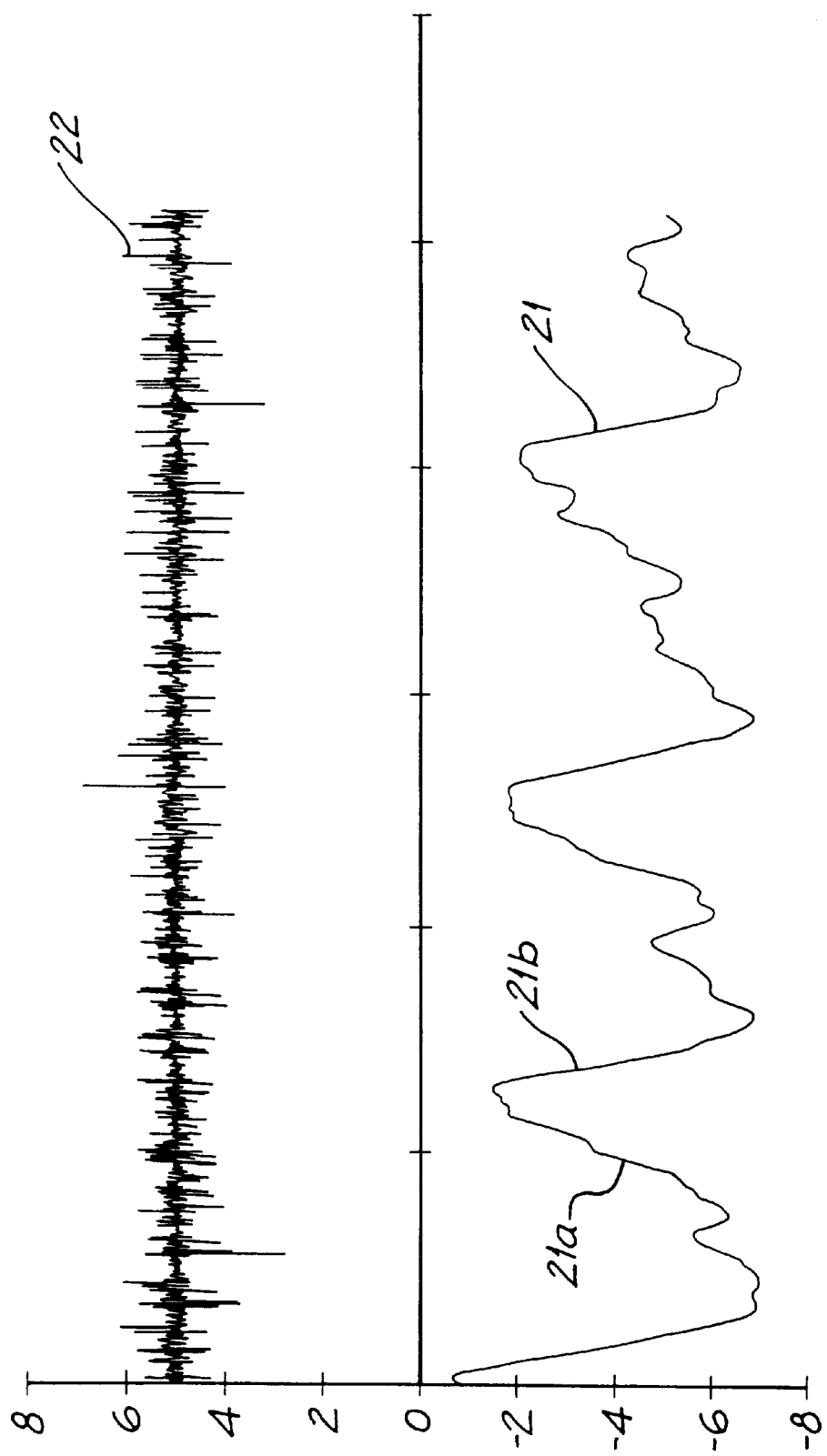
FIG. 2 is an amplitude versus time print-out from a device according to the present invention depicting the output when a patient is not snoring.

A typical output from the device 10 for a sleeping patient undergoing normal respiration is depicted in FIG. 2. The breathing cycle signal generated by device 10 is depicted by curve 21. The curve 21 depicts the quite rhythmical nature of a person's breathing cycle that can be expected during sleep with portion 21a representative of inspiration and portion 21b representative of expiration. Line 22 depicts the signal generated by the sensor 11 in the frequency range 10–100 Hz. The erratic nature of the output 22 in FIG. 2 is representative of small movements being made by the patient 13. There is, however, no signal being received indicative of the sub-audible vibrations present in the airway during snoring by the patient.

Figure 3:
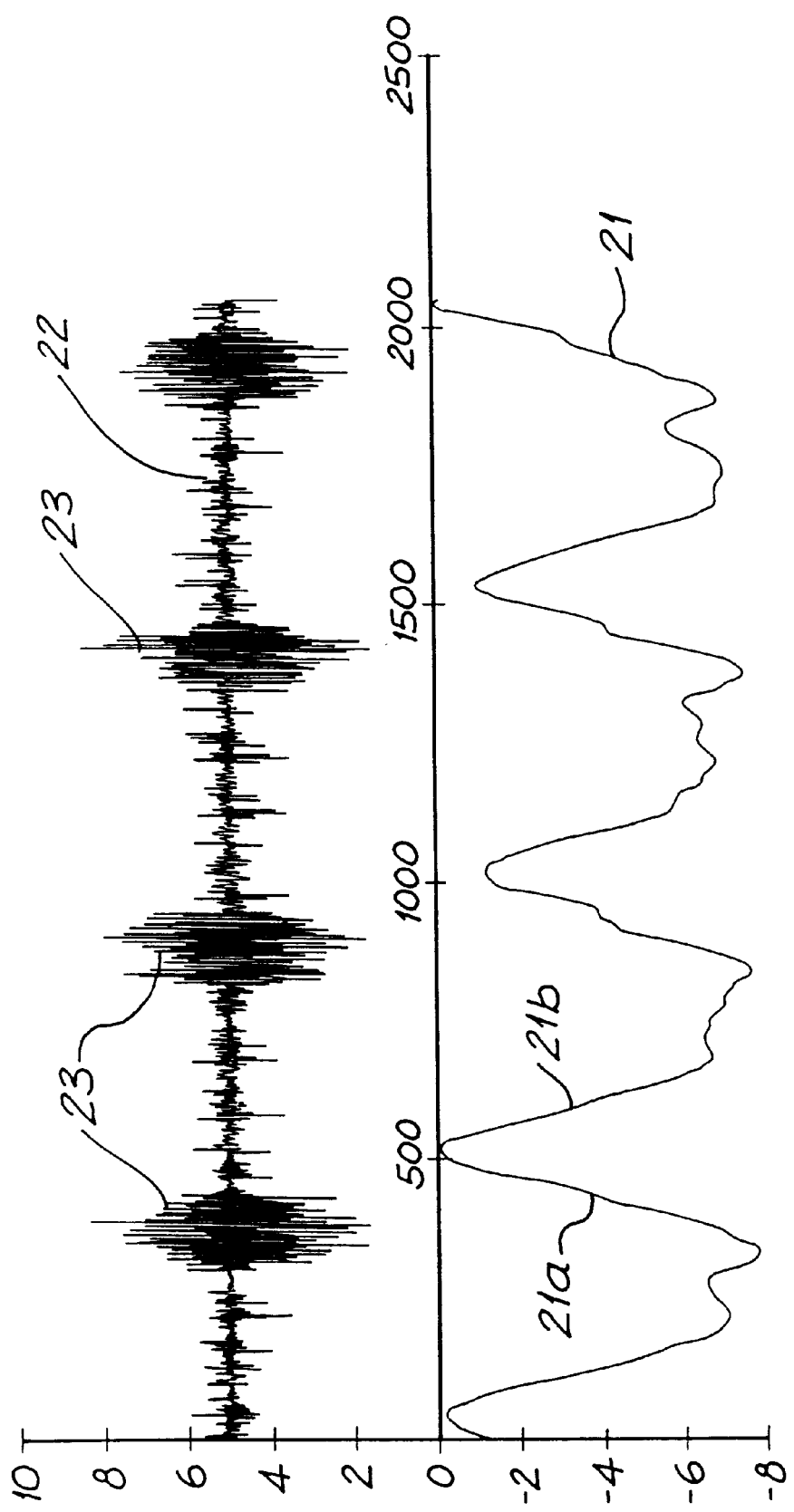
FIG. 3 is an amplitude versus time print-out depicting the output from a snoring patient.
Figure 4:
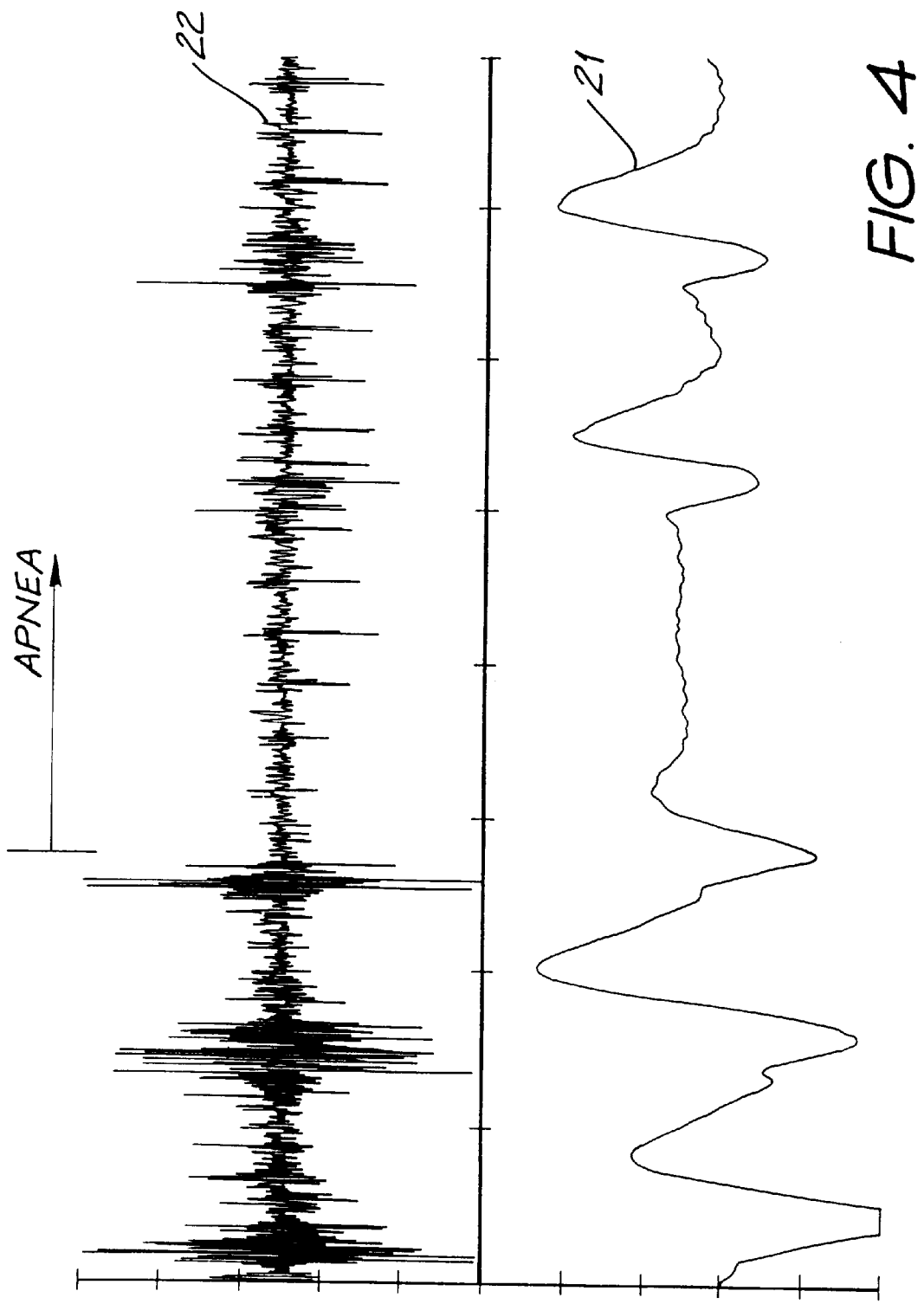
FIG. 4 is an amplitude versus time print-out depicting the output from a patient entering an apnea episode.
Figure 5:
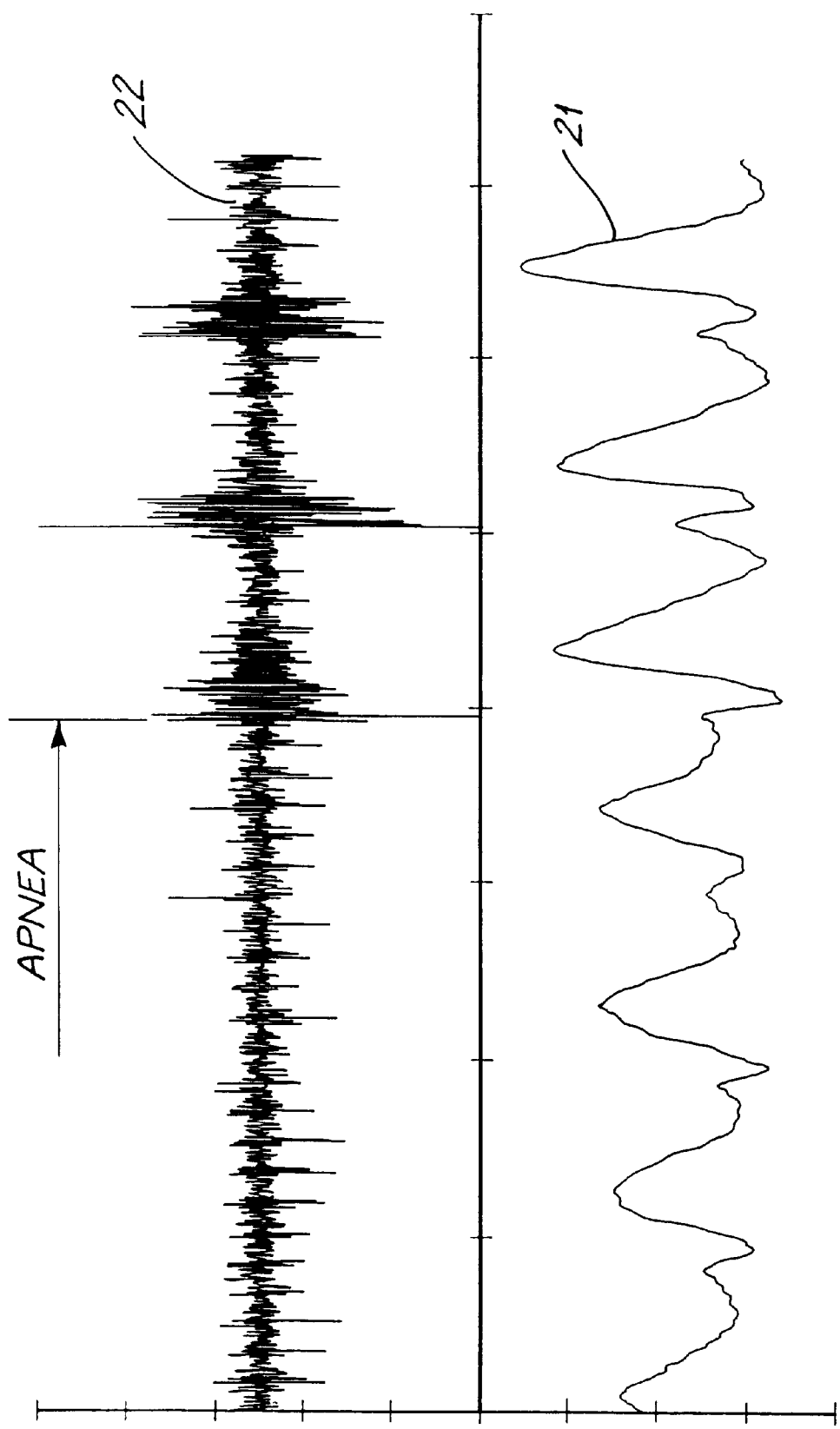
FIG. 5 is an amplitude versus time print-out depicting he output from a patient coming out of an apnea episode.

FIG. 3 represents a typical output from the device 10 for a snoring patient. Once again the rhythmical nature of the patient's breathing cycle is depicted by curve 21. In this case, however, the output from the sensor 11 in the frequency range 10–100 HZ depicted as line 22 reveals relatively short regions of increased amplitude 23 which coincide with inspiration 21a by the patient The regions of increased amplitude 23 represent the sub-audible vibrations present in the airway of the patient 13 during a snore. A clinician reviewing the output depicted in FIG. 3 could conclude that the patient was snoring at the time of this output. As snoring is a diagnostic indication of sleep, the clinician could also conclude that the patient was asleep at the time of this output FIGS. 4 and 5 represent the typical outputs for a patient entering and leaving a sleep apnea episode, respectively. In FIG. 4, a sequence of snores 23 are detected in output 22 followed by no significant signals. Concurrently with the beginning of the region of no snoring, the breathing cycle 21 becomes disrupted followed by a sequence of inspiratory movements which result in no snores occurring. To a trained clinician, the output depicted in FIG. 4 would indicate the occurrence of a sleep apnea episode. This sequence is continued in FIG. 5 where a period of no snores and short inspiratory movements is followed by the resumption of snoring and normal inspiratory movements. The episode of apnea depicted in FIGS. 4 and 5 can in the case of heavy sufferers occur continually throughout the night.

It will be appreciated by persons skilled in the art that numerous variations and/or modifications may be made to the invention as shown in the specific embodiment without departing from the spirit or scope of the invention as broadly described. The present embodiments are, therefore, to be considered in all respects as illustrative and not restrictive.

I claim:

1. A device for detecting the snoring of a patient comprising signal processing means having signal receiving means to receive electrical signals generated by one of a pressure and acceleration detector, the detector being adapted to detect both sub-audible vibrations of a patient's airway which are present during a snore and the patient's breathing cycle, and generate a first electrical signal representative of the sub-audible vibrations and a second electrical signal representative of the patient's breathing cycle.

2. The device of claim 1 wherein the sub-audible vibrations have a frequency in a range of about 10–100 Hz.

3. The device of claim 1 wherein the device includes an output means for producing an output indicative of the sub-audible vibrations of the patient's airway.

4. The device of claim 1 wherein the breathing cycle has a frequency greater than about 0 Hz and not exceeding about 2 Hz.

5. The device of claim 1 wherein the device includes an output means for producing an output indicative of the sub-audible vibrations and the patient's breathing cycle.

6. The device of claim 1 wherein the detector is capable of generating a third electrical signal representing of movement of the patient.

7. The device of claim 6 wherein the device includes output means for producing an output indicative of the sub-audible vibrations of the airway, the patient's breathing cycle and the movement of the patient.

8. The device of claim 7 wherein the signal processing means includes a comparator means for comparing an occurrence of the first electrical signal with the second and third electrical signals and produces an output indicative of the comparison.

9. The device of claim 1 wherein the detector is selected from the group consisting of a pressure detector comprising a piezoelectric transducer and an accelerometer comprising an integrated circuit containing a floating piezoelectric transducer.

10. The device of claim 9 wherein the piezoelectric transducer is a piezoelectric synthetic plastics material.

11. The device of claim 10 wherein the piezoelectric synthetic plastics material is polyvinylidene fluoride (PVDF).

12. The device of claim 10 wherein the piezoelectric transducer is located above or below a mattress on which the patient can sleep.

13. The device of claim 1 wherein the signal processing means further includes a comparator means for comparing an occurrence of the first electrical signal with the second electrical signal and produces an output indicative of the comparison.

14. The device of claim 1 wherein the signal processing means analyses the first and second electrical signals for an occurrence of signals characteristic of episodes of obstructive sleep apnea.

15. The device of claim 1 wherein the device includes means for removing unwanted signals.

16. The device of claim 1 wherein the signal receiving means is arranged to receive signals from at least one sound transducer located near the patient.

17. The device of claim 16 wherein the signal processing means includes means for utilizing the signals received from the sound transducer to remove unwanted signals produced by the detector.

18. A method for detecting the snoring of a patient comprising the steps of placing a pressure or acceleration detector in position relative to a patient for a period of time while the patient is asleep, the detector being adapted to detect both sub-audible vibrations of a patient's airway which are present during a snore and the patient's breathing cycle, and producing from the detector a first electrical signal representative of the sub-audible vibrations and a second electrical signal representative of the patient's breathing cycle.

19. The method of claim 17 further comprising the step of producing an output indicative of the sub-audible vibrations of the patient's airway.

20. The method of claim 18 further comprising the step of producing an output indicative of the sub-audible vibrations of the patient's airway and the patient's breathing cycle.

21. The method of claim 18 further comprising the step of producing from the detector a third electrical signal representative of movement of the patient.

22. The method of claim 21 further comprising the step of producing an output indicative of the sub-audible vibrations of the patient's airway, the patient's breathing cycle and the movement of the patient.

23. The method of claim 18 wherein the first and second electrical signals are compared to produce an output from the comparison that confirms or precludes the detection of snoring by the detector.

24. The method of claim 23 wherein the output is used to control the operation of a continuous positive airway pressure device.

25. The method of claim 18 wherein the first and second electrical signals are analysed for episodes of signals characteristic of obstructive sleep apnea.

26. The method of claim 18 wherein the first electrical signal is produced throughout the sleeping time of the patient.

* * * * *